United States Patent [19]
Gragg

[11] Patent Number: 5,688,236
[45] Date of Patent: Nov. 18, 1997

[54] TOPICAL HYPERBARIC DEVICE FOR TREATING SKIN DISORDERS

[75] Inventor: Stephen R. Gragg, Northbrook, Ill.

[73] Assignee: Stephen's Medical, Inc., Glenview, Ill.

[21] Appl. No.: 649,804

[22] Filed: May 17, 1996

[51] Int. Cl.$^6$ ................................................ A61M 37/00
[52] U.S. Cl. ........................... 604/23; 604/305; 604/308
[58] Field of Search ........................ 604/23, 289, 305,
604/308; 606/201; 602/13; 128/202.12,
205.13, 205.22, 205.24, 205.26; 623/8

[56] References Cited

U.S. PATENT DOCUMENTS

| | | |
|---|---|---|
| 1,525,605 | 1/1925 | Dry . |
| 2,085,296 | 6/1937 | Carey . |
| 2,463,400 | 3/1949 | Lowe . |
| 2,481,427 | 9/1949 | Hunter . |
| 4,206,524 | 6/1980 | Cook . |
| 4,224,941 | 9/1980 | Stivala . |
| 4,328,799 | 5/1982 | LoPiano . |
| 4,474,571 | 10/1984 | Lasley . |
| 4,480,638 | 11/1984 | Schmid ........................... 604/23 |
| 4,509,513 | 4/1985 | Lasley ........................ 128/202.12 |
| 4,685,447 | 8/1987 | Iverson et al. .................... 623/11 |
| 4,778,446 | 10/1988 | Jensen ............................ 604/27 |
| 4,801,291 | 1/1989 | Loori ............................. 604/23 |
| 4,825,488 | 5/1989 | Bedford . |
| 4,847,933 | 7/1989 | Bedford . |
| 4,914,766 | 4/1990 | Moore ............................. 5/432 |
| 5,046,205 | 9/1991 | Garciá . |
| 5,053,011 | 10/1991 | Strobel et al. ................... 604/142 |
| 5,107,557 | 4/1992 | Boyd ............................. 5/541 |
| 5,133,096 | 7/1992 | Neumann . |
| 5,154,697 | 10/1992 | Loori . |
| 5,325,551 | 7/1994 | Tappel et al. . |

*Primary Examiner*—Michael Buiz
*Assistant Examiner*—Nancy Connolly Mulcare
*Attorney, Agent, or Firm*—Leydig, Voit & Mayer, Ltd.

[57] ABSTRACT

A topical hyperbaric therapy device is provided for treating skin disorders and for administering pressurized therapeutic gas (e.g., hyperbaric oxygen) to an afflicted region of a patient's skin. In particular, the topical hyperbaric therapy device of the present invention comprises an inflatable and generally toroidal-shaped tube having a top portion, a bottom portion, and an open interior portion. In addition, a pliable pad member is sealably joined to the bottom portion of the tube. In use, the pliable pad member and the open interior portion of the tube define an enclosed chamber when the tube is inflated and top portion of the tube is sealably constrained against the patient's skin. The topical hyperbaric therapy device also includes an inlet port for supplying pressurized therapeutic gas to the enclosed chamber, and an outlet port for venting pressurized therapeutic gas from the enclosed chamber once the pressure therein becomes greater than a predetermined level.

20 Claims, 2 Drawing Sheets

5,688,236

TOPICAL HYPERBARIC DEVICE FOR TREATING SKIN DISORDERS

TECHNICAL FIELD OF THE INVENTION

The present invention relates generally to a device for treating skin disorders and, more particularly, to a topical hyperbaric therapy device for administering pressurized oxygen in the treatment of decubitus ulcers (i.e., pressure sores).

BACKGROUND OF THE INVENTION

As is known in the art, the treatment of many types of skin disorders—including wounds, sores, lesions, burns, ulcerations, and the like—is promoted by applying hyperbaric (i.e., pressurized) oxygen to the afflicted region of the patient's skin. In particular, it is known that the application of hyperbaric oxygen facilitates the healing of various skin lesions by suppressing bacterial growth, by promoting tissue granulation, and by accelerating epithelization. It is also known that the application of hyperbaric oxygen is particularly beneficial in the treatment of decibutus ulcers (i.e., pressure sores).

There are several known prior art devices for administering hyperbaric oxygen to a patient's skin. Such devices fall into two general categories: (1) larger, non-topical devices (i.e., devices which encompass the patient's entire body); and (2) smaller, topical devices (i.e., portable devices which encompass only a localized region of the patient's skin). Both topical and non-topical prior art devices, however, have undesirable attributes.

For instance, non-topical prior art devices are not only expensive to manufacture, but are also costly to operate and maintain. Non-topical prior art devices, because of their larger size, also require a substantial amount of oxygen to operate. In addition, because non-topical prior art devices typically operate at extreme pressure levels (e.g., two atmospheres and above), they also tend to subject the patient to more serious adverse reactions, including hearing problems, visual problems, and possible seizures.

Even though topical prior art devices are less expensive and smaller than non-topical prior art devices, they too suffer from several shortcomings. In particular, topical prior art devices are uncomfortable to use. For example, in order to minimize oxygen leakage between the patient's skin and the device itself, non-topical prior art devices typically require: (1) an adhesive sealing material (see, e.g., U.S. Pat. Nos. 5,154,697 (Loori); and 4,224,941 (Stivala)); and/or (2) a strap or belt (see, e.g., U.S. Pat. No. 4,474,571 (Lasley)). The use of an adhesive sealing material is particularly uncomfortable because it clings to the hair on the patient's body, which makes removing the device extremely painful. Adhesive sealing materials are also deficient because they tend to deteriorate over time.

SUMMARY OF THE INVENTION

Accordingly, a primary object of the present invention is to provide a topical hyperbaric therapy device for use in treating skin disorders.

A more specific object of the present invention is to provide a topical hyperbaric therapy device for use in healing and impeding the recurrence of decibutus ulcers (i.e., pressure sores).

Another object of the present invention is to provide a topical hyperbaric therapy device which more reliably administers pressurized therapeutic gas (e.g., oxygen) to an afflicted region of a patient's skin.

A further object of the present invention is to provide a topical hyperbaric therapy device which comfortably supports and reduces the pressure on the afflicted region of the patient's skin.

A related object of the present invention is to provide a topical hyperbaric therapy device which removes the afflicted region of the patient's skin from direct contact with an external surface (e.g., a bed).

Another related object of the present invention is to provide a topical hyperbaric therapy device which minimizes surface friction between the afflicted region of the patient's skin and the external surface.

An additional object of the present invention is to provide a topical hyperbaric therapy device which self-seals against the patient's skin when the patient lays on it.

A related object of the present invention is to provide a topical hyperbaric therapy device which comfortably seals against the patient's skin without using adhesive materials or straps.

Another related object of the present invention is to provide a topical hyperbaric therapy device which minimizes leakage of pressurized gas or oxygen therefrom.

A further related object of the present invention is to provide a topical hyperbaric therapy device which provides a stronger and more reliable seal by utilizing the patient's body weight.

Still another related object of the present invention is to provide a topical hyperbaric therapy device which maintains an increased oxygen pressure level around the afflicted region of the patient's skin thereby inducing deeper, more thorough tissue perfusion.

An additional object of the present invention is to provide a topical hyperbaric therapy device which improves patient therapy compliance by allowing patients to comfortably receive prolonged treatments (e.g., 90 minutes) without changing their normal position in bed.

Another object of the present invention is to provide a topical hyperbaric therapy device which is either reusable or disposable.

Still another object of the present invention is to provide a topical hyperbaric therapy device which operates in a safe, simple, and comfortable manner.

Yet another object of the present invention is to provide a topical hyperbaric therapy device having the foregoing characteristics which is not only inexpensive to fabricate, but is also dependable, durable, and convenient to use.

These and other objects of the present invention are attained by means of an inflatable tube or bladder having a top surface, a bottom surface, and an interior space disposed therein. In use, the interior space of the inflatable bladder defines an enclosed chamber when the bladder is inflated and the top surface of the bladder is sealably constrained against the patient's body (e.g., by placing the bottom surface of the inflatable bladder on an external surface, such as a bed, and then distributing the patient's body over the interior space). An inlet port and an outlet port are also provided. In use, the inlet port conveniently supplies therapeutic hyperbaric gas, such as oxygen, to the enclosed chamber. The outlet port automatically vents gas from the enclosed chamber, as a safety precaution, if the pressure therein reaches a predetermined pressure level.

While the present invention will be described and disclosed in connection with a preferred embodiment, the intent is not to limit the present invention to this specific embodiment. On the contrary, the intent is to cover all such alternatives, modifications, and equivalents that fall within the spirit and scope of the present invention as defined by the appended claims.

DETAILED DESCRIPTION OF THE PREFERRED EMBODIMENT

Figure 1:
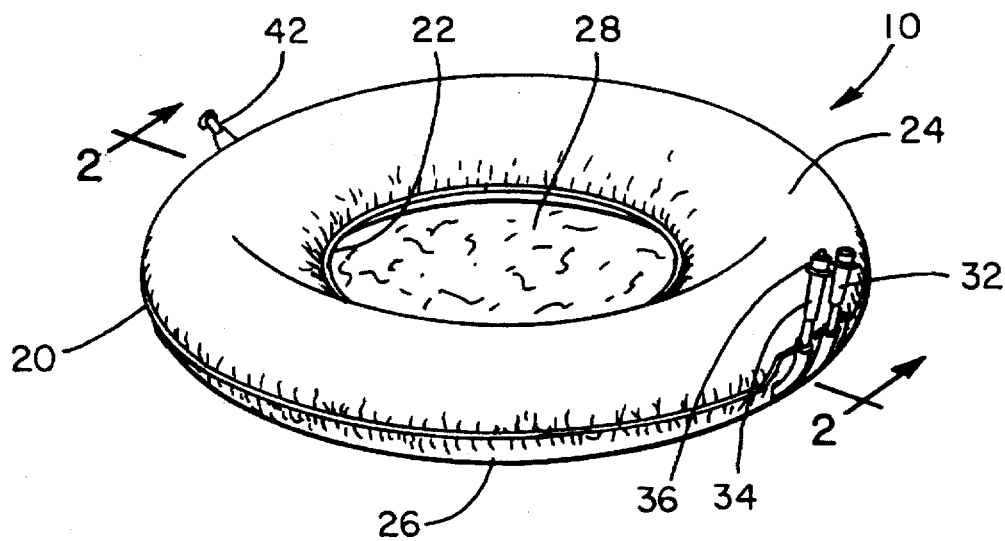
FIG. 1 is a perspective view of a topical hyperbaric therapy device constructed in accordance with the teachings of the present invention.
Figure 3:
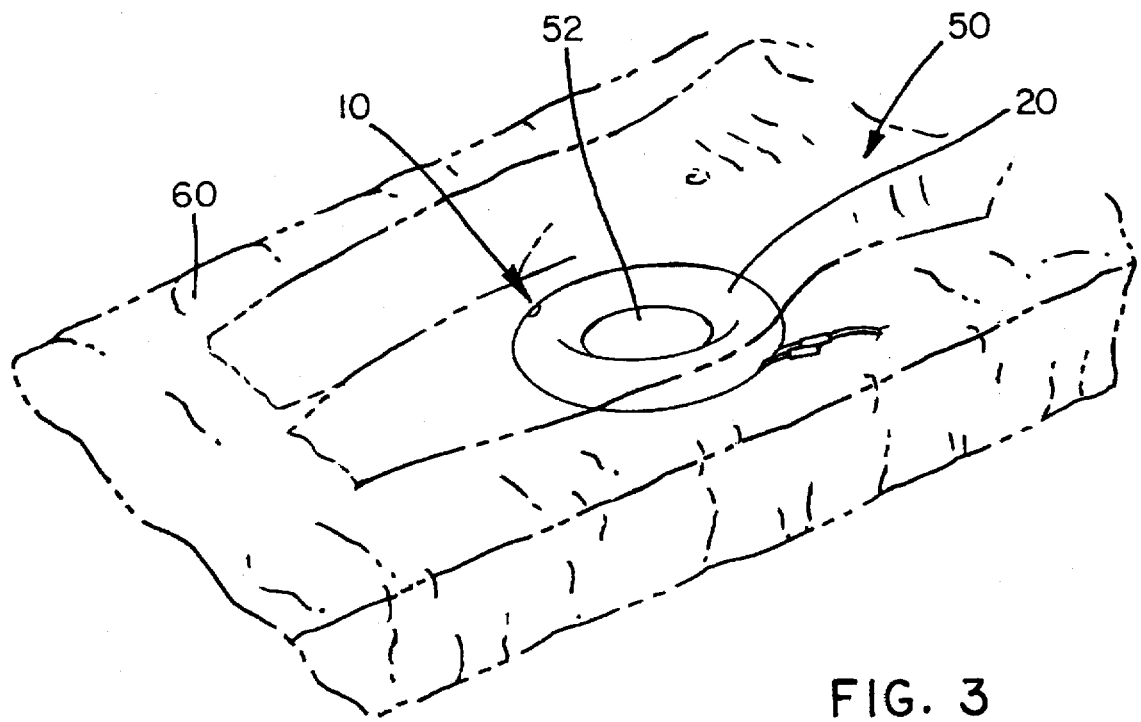
FIG. 3 is a perspective view of the topical hyperbaric therapy device, shown applied to a patient.
Figure 2:
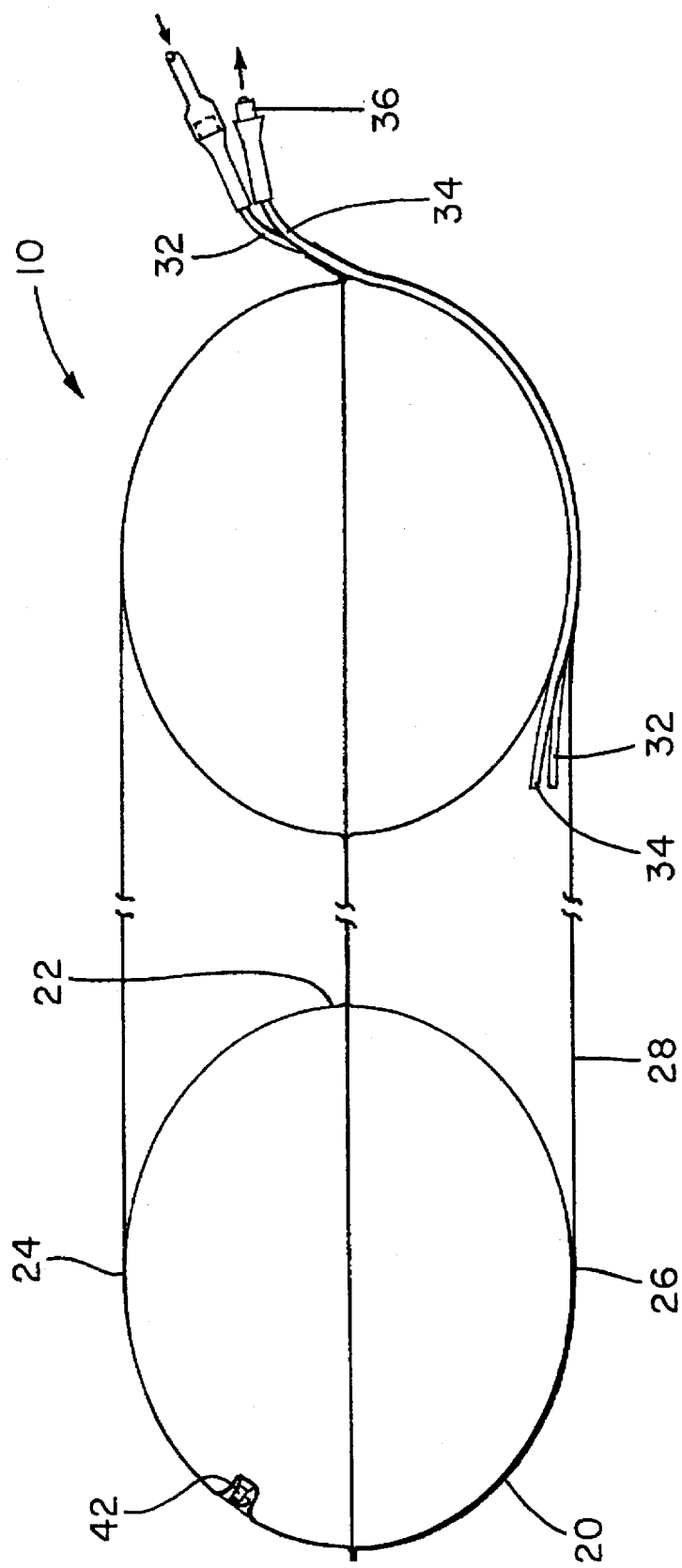
FIG. 2 is a cross-sectional view of the topical hyperbaric therapy device, taken along line 2—2 in FIG. 1.

Referring now to the drawings, there is shown in FIGS. 1-3 a preferred embodiment of a topical hyperbaric therapy device constructed in accordance with the teachings of the present invention and designated generally by reference numeral 10. As best depicted in FIG. 3, the topical hyperbaric device 10 of the present invention is applied directly to a patient 50 in order to treat various types of skin disorders, including wounds, sores, lesions, burns, ulcerations, and the like. It will be understood by those skilled in the art, however, that the topical hyperbaric device 10 of the present invention is especially useful in healing decibutus ulcers (i.e., pressure sores).

In accordance with an important aspect of the present invention, the topical hyperbaric therapy device 10 encapsulates and seals an afflicted region of the patient's skin, designated generally by reference numeral 52 in FIG. 3, so that a suitable therapeutic gas (e.g., hyperbaric oxygen) may be administered directly thereto. Unlike the prior art, however, the topical hyperbaric device 10 of the present invention automatically seals the patient's skin 52 against leakage of gas, without using uncomfortable adhesive materials and/or straps.

As best shown in FIGS. 1 and 2, the topical hyperbaric device 10 of the present invention comprises a inflatable tube or bladder 20 having a top surface 24, a bottom surface 26, and an interior portion (or space) 22 disposed therein. Of course, the interior portion 22 of the tube 20 is most clearly defined after the tube 20 has been fully inflated. Although the tube 20 is typically inflated with air, it may alternatively be inflated with other gaseous or liquid substances.

In order to provide a means for conveniently inflating (and deflating) the tube 20, the tube 20 is provided with a retractable inflation valve 42. In use, the inflation valve 42 not only facilitates inflation (or deflation) of the tube 20, but also provides an added level of comfort for the patient 50. In particular, when the inflation valve 42 is fully extended, as shown in FIG. 1, the tube 20 may be easily inflated (or deflated). Conversely, when the inflation valve 42 is fully retracted (i.e., within the tube 20), as shown in FIG. 2, the patient 50 may recline on the tube 20 without being uncomfortably poked or prodded by the tip of the valve 42.

In the illustrated embodiment, the inflatable tube 20 assumes a generally toroidal configuration after it has been fully inflated. More specifically, the inflated tube 20 depicted in FIGS. 1 and 2 has an outer diameter of approximately 17 inches, an inner diameter of approximately 8 inches, and a height of approximately 3½ inches. A toroidal shape is particularly beneficial because it permits the patient 50 to easily situate the afflicted region of his or her skin 52 over the interior space 22 of the tube 20, as shown, for example, in FIG. 3. It will be appreciated by those skilled in the art, however, that other configurations and sizes may be more appropriate, depending on the nature of the afflicted region of the patient's skin 52 and the contour of the surrounding areas of the patient's body. By way of non-limiting example, a smaller tube 20 having a generally elliptical outer contour may be more suitable for certain applications.

Of course, in order for the tube 20 to be able to support the weight of the patient 50 and remain inflated, it must be fabricated from a non-porous, durable, and resilient material. Plastic materials, including vinyl and the like, are particularly well suited for this purpose.

As shown in FIGS. 1 and 2, the inflatable tube 20 includes a pliable pad or base member 28 which is joined to the bottom surface 26 thereof. In the preferred embodiment, the pad member 28 is fabricated from the same type of material as the inflatable tube 20. The pad member 28 is also integrally attached to the bottom surface 26 of the inflatable tube 20 by a seal which prevents leakage therebetween. It will be appreciated by those skilled in the art that a radio frequency seal, or the like, provides a sufficiently strong and reliable seal.

In accordance with an important aspect of the present invention, the pliable pad member 28 and the interior portion 22 of the tube 20 define an enclosed chamber when the top portion 24 of the tube 20 is sealably constrained against the patient's skin 52, as shown, for example, in FIG. 3. In particular, the enclosed chamber may be formed simply by: (1) placing the bottom portion 26 of the tube 20 on an external surface 60, such as a bed or a wheelchair; and then (2) having the patient 50 recline or sit on the top portion 24 of the tube 20 such that his or her weight is distributed thereon.

Once the inflatable tube 20 is sealably constrained against the patient's skin 52, a suitable therapeutic gas—preferably, hyperbaric oxygen—may be delivered to the enclosed chamber without a significant loss of pressure. Thus, in accordance with certain objects of the present invention, the inflatable tube 20 not only comfortably self-seals against the patient's skin 52, but also minimizes the leakage of pressurized gas therefrom. Of course, in order to be most effective during treatment, the enclosed chamber should be placed adjacent to the afflicted region of the patient's skin 52.

In use, the inflatable tube 20 also lifts or elevates the afflicted region of the patient's skin 52 away from the external surface 60. Thus, in accordance with certain objects of the present invention, the inflatable tube 20 removes the afflicted region of the patient's skin 52 from direct contact with the external surface 60, and also cushions the afflicted region of the patient's skin 52. In this way, the inflatable tube 20 minimizes the amount of surface friction between the afflicted region of the patient's skin 52 and the external surface 60 which helps reduces the recurrence of decibutus ulcers.

Although an inflatable tube having an attached pad member is specifically described and illustrated herein, it will be understood by those skilled in the art that the enclosed chamber may alternatively be formed without the use of a pad member. By way of example, the enclosed chamber could be provided by a non-toroidal tube including a substantially flat bottom surface and a top surface having an interior space disposed therein.

In order to supply pressurized gas to the enclosed chamber, the topical hyperbaric device 10 of the present invention includes an inlet port 32. In the illustrated embodiment, the inlet port 32 comprises a flexible hose or tubing having a first end which is attached to the inflatable tube 20 and a second end which is adapted to be connected to a pressurized gas source (not shown). As best illustrated in FIG. 2, the inlet port 32 is partially disposed between the pliable pad member 28 and the bottom surface 26 of the inflatable tube 20. In this way, a suitable therapeutic gas, such as hyperbaric oxygen, may be conveniently delivered to the enclosed chamber and administered the afflicted region of the patient's skin 52.

The topical hyperbaric device 10 of the present invention also includes an outlet port 34 for venting pressurized gas from the enclosed chamber if, and when, the pressure therein becomes excessive. As most clearly shown in FIG. 2, the outlet port 34 comprises a flexible hose or tubing which includes a spring-activated pressure relief valve 36. Normally, the pressure relief valve 36 is biased closed so that pressurized gas is prevented from escaping the enclosed chamber via the outlet port 34. Like the inlet port 32 described above, the outlet port 34 is also partially disposed between the pliable pad member 28 and the bottom surface 26 of the inflatable tube 20.

In operation, the pressure relief valve 36 provides a dependable means for keeping the pressure within the enclosed chamber at, or near, a predetermined pressure level (e.g., 22 mm Hg). In particular, since the pressure relief valve 36 is biased closed, the gas within the enclosed chamber is normally prevented from escaping through outlet port 34. If, however, the pressure within the enclosed chamber becomes greater than the predetermined pressure level, the pressure relief valve 36 is urged open and the gas within the enclosed chamber is allowed to escape via outlet port 34. Once the pressure within the enclosed chamber drops below the predetermined pressure level, though, the pressure relief valve 36 recloses and the gas within the enclosed chamber is again prevented from escaping through outlet port 34. In this way, the pressure relief valve 36 automatically vents gas from the enclosed chamber once the pressure therein becomes excessive (i.e., greater than the predetermined pressure level). Alternatively, the pressure relief valve 36 could serve as, or be replaced with, a flow control device in order to maintain a substantially uniform flow rate of pressurized gas through the enclosed chamber.

Thus, in accordance with certain objects of the present invention, the topical hyperbaric therapy device 10 described and illustrated herein provides a simple, safe, comfortable, and reliable means for administering pressurized therapeutic gas—and, more particularly, hyperbaric oxygen—to an afflicted region of the patient's skin 52.

In accordance with yet another object of the present invention, the topical hyperbaric therapy device 10 is also relatively inexpensive to fabricate. As such, the topical hyperbaric device 10 of the present invention may either be discarded after use, or deflated, sanitized, and stored, for eventual re-use.

What is claimed is:

1. A self-sealing topical hyperbaric therapy device for administering hyperbaric gas to a region of a patient's skin, said device comprising, in combination:
    an inflatable tube adapted to be inflated with air and having a top portion and a bottom portion, the tube assuming a collapsed configuration wherein the top and bottom portions are substantially adjacent when deflated and assuming an expanded configuration wherein the top and bottom portions are substantially separated when inflated, the expanded configuration of the tube including an open interior space;
    a pliable pad member joined to the bottom portion of the inflatable tube, the pliable pad member and the open interior space of the tube defining an enclosed chamber when the tube is in the expanded configuration and the top portion of the tube is sealably constrained against the patient's skin; and
    an inlet port connected to the inflatable tube for supplying hyperbaric gas to the enclosed chamber.

2. The self-sealing topical hyperbaric therapy device set forth in claim 1, further comprising:
    an outlet port connected to the tube for venting hyperbaric gas from the enclosed chamber once the pressure therein reaches a predetermined level.

3. The self-sealing topical hyperbaric therapy device set forth in claim 2, wherein the outlet port includes a pressure relief valve.

4. The self-sealing topical hyperbaric therapy device set forth in claim 1, wherein the hyperbaric gas is oxygen.

5. The self-sealing topical hyperbaric therapy device set forth in claim 1, wherein the region of the patient's skin is afflicted with a skin disorder.

6. The self-sealing topical hyperbaric therapy device set forth in claim 5, wherein the skin disorder is a decubitus ulcer.

7. The self-sealing topical hyperbaric therapy device set forth in claim 1, wherein the inflatable tube and the pliable pad member are formed of plastic.

8. The self-sealing topical hyperbaric therapy device set forth in claim 1, wherein the inflatable tube and the pliable pad member are formed of vinyl.

9. The self-sealing topical hyperbaric therapy device set forth in claim 1, wherein the pliable pad member is integrally attached to the bottom portion of the inflatable tube.

10. The self-sealing topical hyperbaric therapy device set forth in claim 1, wherein the pliable pad member is integrally attached to the bottom portion of the inflatable tube by a radio frequency seal.

11. The self-sealing topical hyperbaric therapy device set forth in claim 3, wherein the pressure relief valve is spring-activated.

12. The self-sealing topical hyperbaric therapy device set forth in claim 1, wherein the inflatable tube includes a retractable inflation valve.

13. A self-sealing topical hyperbaric therapy device for administering pressurized oxygen to an afflicted region of a patient's body, said device comprising, in combination:
    an inflatable and generally toroidal plastic tube adapted to be inflated with air and having a top surface and a bottom surface, the tube assuming a collapsed configuration wherein the top and bottom surfaces are substantially adjacent when deflated and assuming an expanded configuration wherein the top and bottom surfaces are substantially separated when inflated, the expanded configuration of the tube including a center region;
    a flexible base member sealably joined to the bottom surface of the inflatable tube, the flexible base member and the center region of the tube defining an enclosed sealed chamber when the tube is inflated and is disposed between the patient's body and an external surface, the inflatable tube providing a cushion for the patient when disposed between the external surface and the patient's body;

an inlet port connected to the enclosed sealed chamber for supplying pressurized oxygen thereto; and an outlet port connected to the enclosed sealed chamber for venting pressurized oxygen therefrom once the pressure therein reaches a predetermined pressure level.

14. The self-sealing topical hyperbaric therapy device set forth in claim 13, wherein the region of the patient's skin is afflicted with a decubitus ulcer.

15. The self-sealing topical hyperbaric therapy device set forth in claim 13, wherein the inflatable bladder includes an inflation valve for facilitating inflation and deflation thereof.

16. A self-sealing topical hyperbaric device for administering pressurized gas to a patient's body, said device comprising, in combination:

an inflatable bladder having a top surface and a bottom surface, the bladder assuming a collapsed configuration when deflated and assuming an expanded configuration when inflated, the expanded configuration of the tube including an interior space which defines an enclosed chamber when the top surface of the bladder is constrained against a portion of the patient's body; and an inlet port connected to the inflatable bladder, the inlet port adapted to supply pressurized gas to the enclosed chamber.

17. The self-sealing topical hyperbaric device set forth in claim 16, further comprising:

an outlet port connected to the inflatable bladder for venting pressurized gas from the enclosed chamber once the pressure therein reaches a predetermined level.

18. The self-sealing topical hyperbaric device set forth in claim 16, wherein the pressurized gas is oxygen.

19. The self-sealing topical hyperbaric device set forth in claim 16, wherein the inflatable bladder is formed of plastic.

20. The self-sealing topical hyperbaric device set forth in claim 16, wherein the inflatable bladder includes an inflation valve which facilitates inflation and deflation thereof.

\* \* \* \* \*